(12) United States Patent
Christensen et al.

(10) Patent No.: US 7,790,776 B2
(45) Date of Patent: Sep. 7, 2010

(54) PROCESS AND CATALYST FOR HYDROGENATION OF CARBON OXIDES

(75) Inventors: Claus Hviid Christensen, Lynge (DK); Martin Andersson, Södra Sandby (SE); Arkady Kustov, Moscow (RU); Tue Johannesen, Glostrup (DK); Thomas Bligaard, Kvistgård (DK); Kasper E. Larsen, Copenhagen N (DK); Jens K. Nørskov, Holte (DK); Jens Sehested, Ballerup (DK)

(73) Assignee: Haldor Topsoe A/S, Lyngby (DK)

( * ) Notice: Subject to any disclaimer, the term of this patent is extended or adjusted under 35 U.S.C. 154(b) by 199 days.

(21) Appl. No.: 12/065,166

(22) PCT Filed: Aug. 28, 2006

(86) PCT No.: PCT/EP2006/008395

§ 371 (c)(1),
(2), (4) Date: May 7, 2008

(87) PCT Pub. No.: WO2007/025691

PCT Pub. Date: Mar. 8, 2007

(65) Prior Publication Data

US 2008/0221227 A1    Sep. 11, 2008

(30) Foreign Application Priority Data

Sep. 2, 2005  (DK) .............................. 2005 01224

Jun. 24, 2006 (DK) .............................. 2006 00854

(51) Int. Cl.
*C07C 27/00* (2006.01)
(52) U.S. Cl. ...................................... 518/715; 518/700
(58) Field of Classification Search ................ 518/700, 518/715
See application file for complete search history.

(56) References Cited

U.S. PATENT DOCUMENTS

| 3,876,557 A | 4/1975 | Bland |
| 3,933,883 A | 1/1976 | Parthasarathy |
| 4,255,289 A * | 3/1981 | Balinsky et al. ............. 502/327 |

FOREIGN PATENT DOCUMENTS

FR           863473        4/1941

* cited by examiner

*Primary Examiner*—Jafar Parsa
(74) *Attorney, Agent, or Firm*—Dickstein Shapiro LLP

(57) ABSTRACT

A process for hydrogenation of carbon oxides comprising contacting a gas mixture containing carbon oxides and of hydrogen with a catalyst comprising bimetallic iron-nickel or iron-cobalt alloys as the active catalytic material supported on a carrier of an oxide. The carrier is preferably formed to have a surface area greater than 20 $m^2/g$.

11 Claims, 3 Drawing Sheets

PROCESS AND CATALYST FOR HYDROGENATION OF CARBON OXIDES

BACKGROUND OF THE INVENTION

The present invention concerns a process and a catalyst for the hydrogenation of the carbon oxides carbon monoxide and carbon dioxide. More specifically, this invention relates to a process for reacting or removing carbon oxides by hydrogenation using a catalyst comprising a support and an active component being of the composition of alloys of Ni, Fe and Co metals in oxide or reduced form.

The presence of carbon monoxide in feed gases is undesired in a number of processes.

In a fuel cell, such as a Polymer Electrolyte Membrane Fuel Cell, the presence of carbon monoxide is very critical since it can poison the noble metal electrodes used in fuel cells and therefore reduce their effectiveness.

Preferably, the CO concentration for fuel cell feed should be less than 100 ppm, more preferably less then 50 ppm. However, the initial concentration of CO, as received from the fuel processor, can exceed 1 wt %. Therefore, further reduction of CO concentration is required. Some of the typical methods for reducing CO concentration are selective catalytic oxidation of CO, pressure swing adsorption, hydrogen separation by membrane and methanation of CO.

Similarly, in ammonia production plants, the presence of CO is also highly undesirable in the ammonia synthesis reactor and the carbon oxide concentrations should usually be reduced to values as low as 5-10 ppmv.

Reacting carbon monoxide and carbon dioxide with hydrogen may also be used in the preparation of methane/synthetic natural gas (SNG). SNG can be produced by gasification of biomass or coal and subsequent methanation.

Methanation is a process where carbon oxides are reacted with hydrogen in the presence of a catalyst to produce methane and possibly smaller amounts of other lower hydrocarbons and water. In the known methanation processes, precious metals supported on a carrier as $Al_2O_3$, $SiO_2$ or $TiO_2$ have been used as a catalyst for CO methanation (U.S. Pat. No. 3,615,164 and WO 01/64337). These catalysts are usually able to reduce CO concentrations to values of about 500-800 ppm. Nickel-alumina catalysts, which are presently used in conventional methanation processes, contain large proportions of nickel, generally in excess of about 20 wt %. This requirement places certain limitations on practical methods for manufacturing such catalysts. In ammonia plants, methanation is mainly performed in the temperature range of 250° C. to 350° C. in the presence of $Ni/Al_2O_3$ catalysts. Modifications of such catalysts are desirable to achieve reduction and reaction at relatively lower temperatures than in the conventional design.

Alloying an active metal with a second active or inactive metal can change the catalytic performance drastically. For example with a monometallic iron catalyst and bimetallic copper-iron catalysts (E. Boellard, F. Th. van Scheur, A. M. van der Kraan, J. W. Geus, Appl Catal. A 171 (1998) 333. It has further been demonstrated that the reduction profile, carbon monoxide chemisorption properties and the Fischer-Tropsch activity were substantially altered by adding copper to the iron phase.

French patent application FR 863473-A describes a process for the production of hydrocarbons by hydrogenation of carbon monoxide in which the catalyst contains iron and nickel with an atomic ratio of 1:1.

Patent application US 2005/0096211 describes a catalyst for fuel cell applications, which is highly selective in CO methanation, prevents the conversion of $CO_2$ into CO and suppresses $CO_2$ methanation. The catalyst comprises a metal selected from the group consisting of ruthenium, nickel, iron, cobalt, lead, tin, silver, iridium, gold, copper, manganese, zinc, zirconium, molybdenum, other metals that form metal-carbonyl species and combinations thereof on a support.

SUMMARY OF THE INVENTION

We have found that the activity in the methanation of carbon monoxide and dioxide to methane could be improved by alloying iron with nickel within specific ranges of the metals.

Pursuant to the above finding, the present invention provides a process for hydrogenation of carbon oxides comprising contacting a gas mixture containing carbon oxides and hydrogen with a catalyst comprising bimetallic iron-nickel alloy as the active catalytic material supported on a carrier of an oxide, wherein the iron-nickel atomic ratio is between 0.1 and 0.8.

In its broadest scope the invention encompasses the novel catalyst product. Accordingly, we provide a catalyst for the hydrogenation of carbon oxides comprising bimetallic iron-nickel alloy as the active catalytic material supported on a carrier of an oxide, wherein the iron-nickel atomic ratio is between 0.1 and 0.8.

In a preferred embodiment of the invention the iron-nickel atomic-ratio is between 0.1 and 0.7, such as between 0.1 and 0.6, preferably between 0.1 and 0.5, more preferably between 0.2 and 0.5, which results in a surprisingly high CO hydrogenation activity (methanation activity) and thereby high conversion rates of carbon oxides. Most preferably, the iron-nickel atomic ratio is about 0.3 such as 0.35, whereby the achieved methanation activity is even higher.

We have found that the activity in the methanation of carbon monoxide and dioxide to methane could also be improved by alloying iron with cobalt within specific ranges of the metals. Hence we provide also a process for hydrogenation of carbon oxides comprising contacting a gas mixture containing carbon oxides and hydrogen with a catalyst comprising bimetallic iron-cobalt alloy as the active catalytic material supported on a carrier of an oxide, wherein the iron-cobalt atomic ratio is between 0.05 and 2.

The invention encompasses also this novel catalyst product. Accordingly, we provide a catalyst for the hydrogenation of carbon oxides comprising bimetallic iron-cobalt alloy as the active catalytic material supported on a carrier of an oxide, wherein the iron-nickel atomic ratio is between 0.05 and 2.

In a preferred embodiment of the invention the iron-cobalt atomic-ratio is between 0.1 and 1, such as between 0.1 and 0.9, or between 0.1 and 0.8, preferably between 0.1 and 0.5, more preferably between 0.2 and 0.5, which results in a surprisingly high CO hydrogenation activity (methanation activity) and thereby high conversion rates of carbon oxides. Most preferably the iron-cobalt atomic ratio is about 0.3, such as 0.35 whereby the achieved methanation activity is even higher.

We have also found that the selectivity to methane and methanation activity in a process for hydrogenation of carbon oxides where the catalyst comprises bimetallic iron-nickel, cobalt-nickel or iron-cobalt alloys is influenced by the pressure employed in the reaction. Accordingly we also provide a process for hydrogenation of carbon oxides comprising contacting a gas mixture containing carbon oxides and hydrogen with a catalyst comprising bimetallic iron-nickel, cobalt-nickel or iron-cobalt alloys as the active catalytic material supported on a carrier of an oxide, wherein the total pressure is above 20 bar, more preferably in the range 20 to 80 bar most preferably between 30 and 60 bar, such as about 30 bar.

The nickel-cobalt atomic ratio is preferably between 0.3 and 3.

The carrier of an oxide which functions as the support of the catalytic material (the carrier) is preferably formed to have a surface area greater than 20 m²/g.

In this specification the terms carrier and support are used interchangeably.

Preferably, in said gas mixture containing carbon oxides and hydrogen there is a stoichiometric excess of hydrogen, normally well above the stoichiometric amount. By stoichiometric amount is meant the exactly amount of hydrogen required for complete conversion of the carbon oxides carbon monoxide or carbon dioxide to methane according to the reactions $CO+3H_2 \rightarrow CH_4+H_2O$ and $CO_2+4H_2 \rightarrow CH_4+2H_2O$.

As used herein the term carbon oxides is used to encompass the components carbon monoxide, carbon dioxide or mixtures of both.

The catalysts for use in the invention comprise elements selected from the group consisting of nickel, iron and cobalt on a support having a regular lattice structure and selected from the group of oxides, typically $MgAl_2O_4$, $Al_2O_3$, $SiO_2$, $ZrO_2$, $TiO_2$ and mixtures thereof. Other suitable supports include cerium oxide and magnesium oxide which may or may not be used in combination with $MgAl_2O_4$, $Al_2O_3$, $SiO_2$, $ZrO_2$, $TiO_2$. The resulting bimetallic catalyst is capable of hydrogenating carbon oxides using $H_2$ much more effectively than traditional monometallic Ni-based catalysts or alloys of Ni, Fe and Co metals according to the prior art.

Particularly high conversion rates of carbon oxides are obtained according to another embodiment of the invention in which the iron-nickel or iron-cobalt atomic ratio is between 0.1 and 0.8, such as between 0.1 and 0.7, or between 0.1 and 0.6, preferably between 0.2 and 0.5, most preferably at about 0.3, and the process is conducted at a pressure of above 20 bar, more preferably in the range 20 to 80 bar, most preferably at a pressure of between 30 and 60 bar such as about 30 bar. Hence, by the invention we also provide a process for hydrogenation of carbon oxides comprising contacting a gas mixture containing carbon oxides and hydrogen with a catalyst comprising bimetallic iron-nickel alloy or iron-cobalt alloy as the active catalytic material supported on a carrier of an oxide, wherein the total pressure is above 20 bar and the iron-nickel atomic ratio is between 0.1 and 0.8. In a preferred embodiment we provide a process for hydrogenation of carbon oxides comprising contacting a gas mixture containing carbon oxides and hydrogen with a catalyst comprising bimetallic iron-nickel alloy or iron-cobalt alloy as the active catalytic material supported on a carrier of an oxide, wherein the total pressure is about 30 bar and the iron-nickel atomic ratio is about 0.3.

The process according to the invention is suitable for the methanation of carbon oxides at high CO-pressures, such as under Fischer-Tropsch conditions (for production of hydrocarbons) and especially at low CO-pressures, where carbon monoxides have to be removed for Polymer Electrolyte Membrane (PEM) fuel cell applications, as well as for the reduction of carbon monoxide from synthesis gas used in the production of ammonia and not least for the removal of carbon oxides during the production of Synthetic Natural Gas (SNG). In the latter, carbon oxides are gradually removed from the gas by passing it through a number of reactors arranged in series. Normally the gas entering the first reactor contains about 50 vol. % $H_2$ and 16-17 vol. % carbon oxides, while in the last reactor, often the fourth reactor, the content of $H_2$ in the entering gas is about 4 vol. % and the content of carbon oxides may be as low as 1.2 vol. %. Methanation activity is therefore especially required in the last reactor where small amounts of remaining carbon oxides in the gas still have to be removed.

Hence the process and catalyst of the invention are particularly effective (high methanation activity) at low CO-pressure conditions, wherein the concentration of carbon oxides is below 5 vol. % and the hydrogen concentration is in the range 1 to 10 vol. %, often about 4 vol. % hydrogen, such as in the production of Synthetic Natural Gas. The process and catalysts of the invention are also effective at low CO-pressure conditions wherein the concentration of carbon oxides is below 5 vol. % and the hydrogen concentration is above 40 vol. %, such as in the reduction of carbon monoxide from synthesis gas for the production of ammonia synthesis gas and/or the removal of carbon oxides in fuel cell applications.

DETAILED DESCRIPTION

Figure 1:
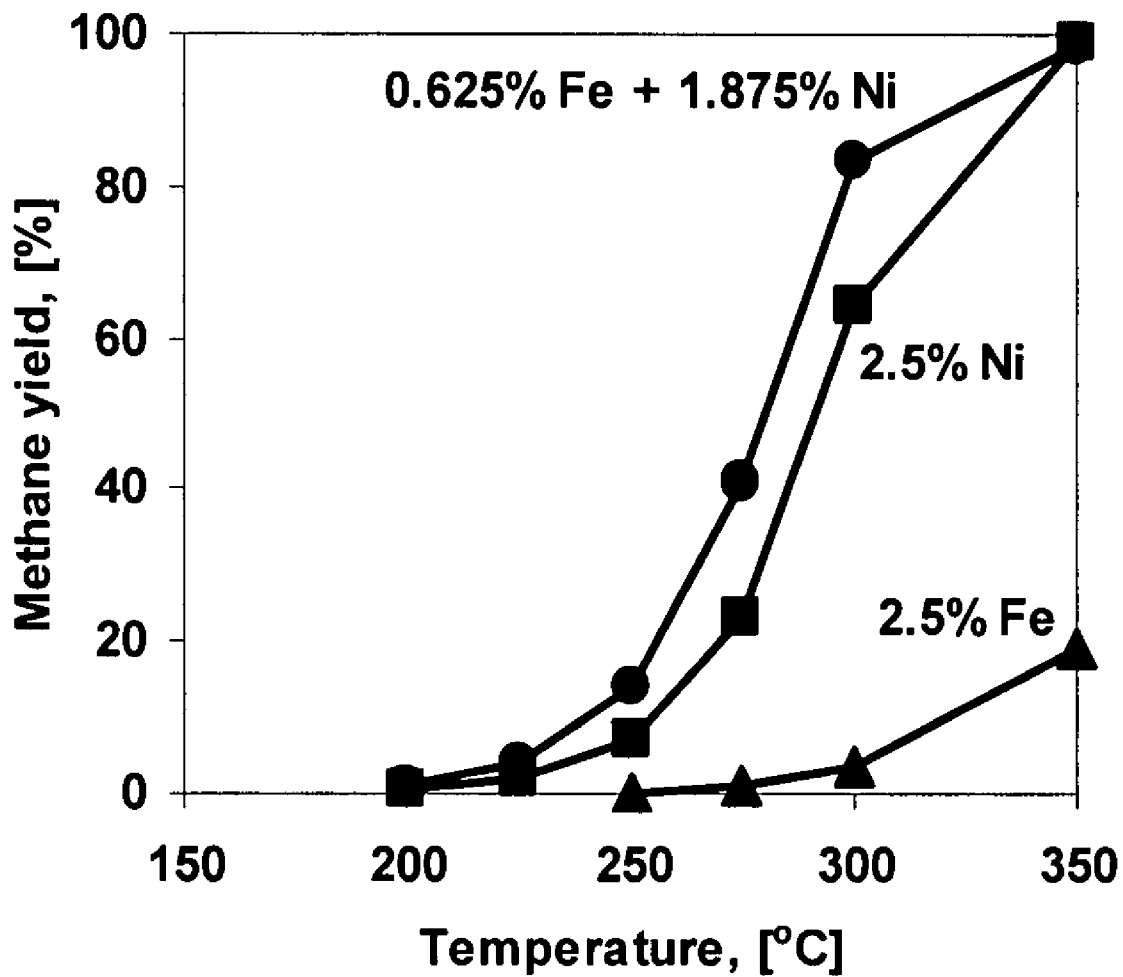
FIG. 1 is a graphical presentation of the CO methanation activity of a mixed Ni—Fe catalyst made in accordance with the present invention and compared with the pure Ni or Fe containing catalysts having the same total metal concentration.
Figure 2:
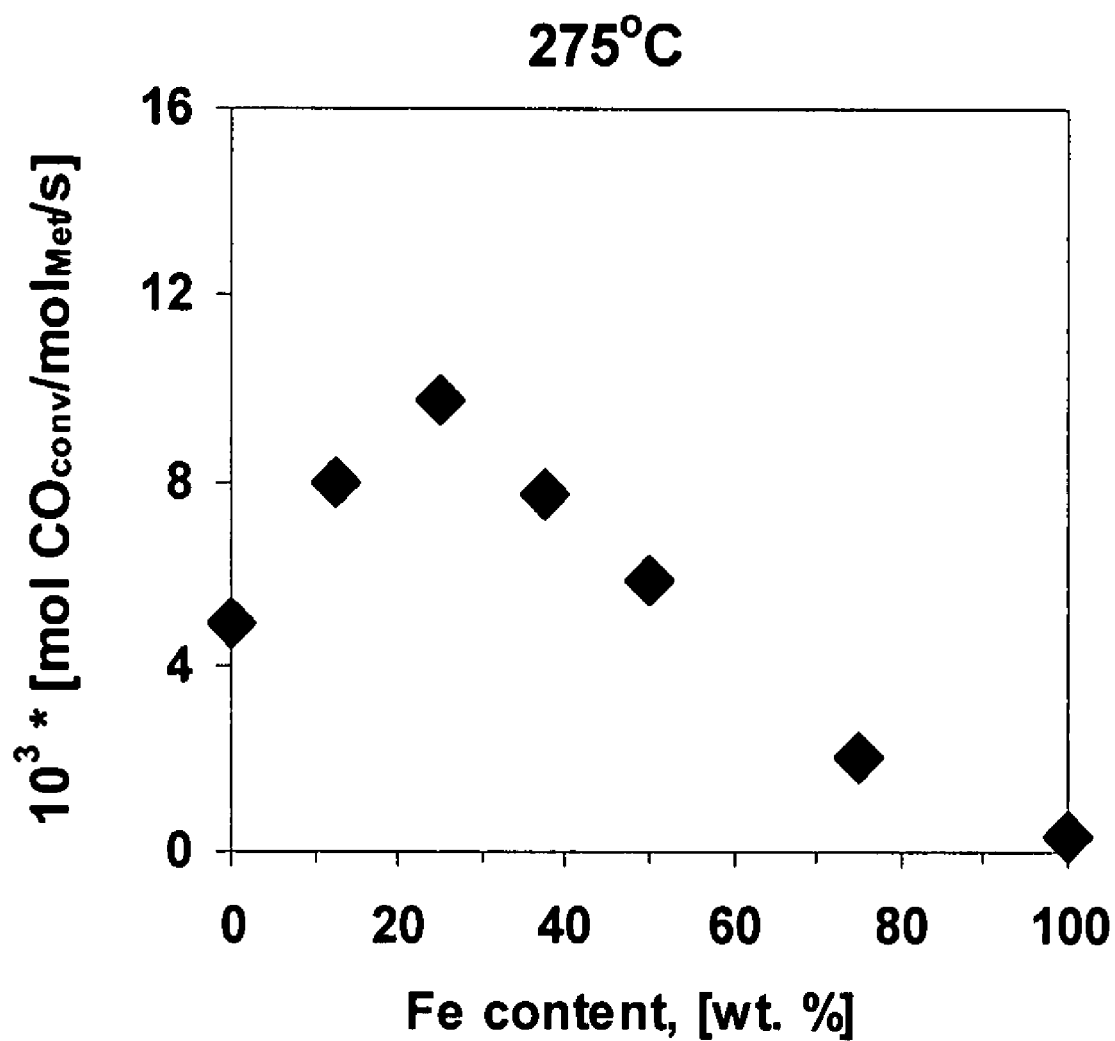
FIG. 2 is a graphical presentation of the CO hydrogenation activity for iron-nickel catalysts made in accordance with the present invention with various metal mixing compositions. The total metal loading is the same for all presented catalyst and is about 2.5 wt %, but it can easily be increased to above 25 wt %.

The present invention will be described herein through exemplary embodiments, figures and examples. Any embodiments, figures, examples and related data presented here are given just to exemplify the principles of the invention and are not intended to limit the scope of the invention.

The metal may be added to the support by any means known in the art, such as, without limitations, impregnation, incipient wetness impregnation, immersion and spraying. The metal nitrates utilized herein can be substituted by any of the well-known water soluble salts or complexes that decompose to oxides when heated in air. Hence, in another embodiment of the invention the bimetallic catalyst is impregnated onto the carrier using precursors that transform into oxide upon heating in air. The sequence of the impregnation of support by metal components to obtain bimetallic catalysts may also be altered in a wide range.

The catalyst may be used in exemplary process for removing or substantially reducing the quantity of carbon monoxide in a mixture of gases containing methane, hydrogen, carbon dioxide, carbon monoxide and water. The process may be used to pass a mixture of gases over the catalyst at a temperature below the temperature at which the water shift reaction occurs and above the temperature at which selective methanation of carbon monoxide occurs.

In the catalyst the total metal loading as defined by the content of bimetallic active catalytic material is preferably about 2.5 wt %, but it may also be increased to 10, 20, 25, 30, 35, 40 wt % and even up to 50 wt %. Hence, according to the invention the content of bimetallic active catalytic material is between 2 wt % and 50 wt %. Higher metal loading enables a higher methanation activity.

A preferred support (carrier) is the spinel-type $MgAl_2O_4$, which may be in the form of spherical pellets or extruded cylindrical ring particles as known in the art. Extruded rings have normally an outer diameter of 5 mm and inner diameter of 2.5 mm and aspect ratio of 2 to 10. Accordingly, the particle size of the particles may vary from 0.10 mm to 10 mm, with preferred sizes (outer diameter) of about 5 mm. The particle size of the support may also be in the range from 0.10 mm to 1 mm, more preferably from 0.25 mm to 0.5 mm and the pore volume in the range of 0.1 $cm^3/g$ to 1.0 $cm^3/g$, preferably about 0.7 $cm^3/g$. The surface area as described above is preferably above 20 $m^2/g$, more preferably about 70 $m^2/g$. Another preferred support is $Al_2O_3$ which may also be in the form of spherical pellets or extruded cylindrical ring particles as known in the art. Extruded rings have normally an outer diameter of 5 mm and inner diameter of 2.5 mm and aspect ratio of 2 to 10. The particle size of the particles may thus vary from 0.10 mm to 10 mm, with preferred sizes (outer diameter) of about 5 mm. The particle size of the support may also vary from 0.10 mm to 1 mm, preferably from 0.25 mm to 0.5 mm and the pore volume in the range 0.1 $cm^3/g$ to 1.0 $cm^3/g$, preferably about 0.7 $cm^3/g$ and with surface area in the range 100-200 $m^2/g$, preferably 150 $m^2/g$. Yet another preferred support is the silica oxide $SiO_2$ having similar particle size and pore volume as for $MgAl_2O_4$ and $Al_2O_3$ and with surface area in the range 200-400 $m^2/g$, preferably 300 $m^2/g$. The use of $Al_2O_3$ instead of $MgAl_2O_4$ enables normally a higher selectivity to methane, but the CO-conversion (methanation activity) is normally higher when using $MgAl_2O_4$ as carrier. Suitable mixtures of $MgAl_2O_4$ and $Al_2O_3$ may be prepared in order to find a carrier for which both selectivity to methane and CO-conversion are sufficiently high.

The process and catalysts of the invention may operate under a wide range of temperatures, but the catalysts are particularly suitable under conditions where the reaction temperature is between 200 and 600° C., preferably between 200 and 400° C., more preferably above 250° C., such as 275 or 300 or 350° C. Higher temperatures enable higher CO-conversions (higher methanation activity).

Best performance in terms of methanation activity and selectivity to methane are obtained for catalysts comprising bimetallic iron-nickel alloys as the active catalytic material supported on a carrier of an oxide, wherein the iron-nickel atomic ratio is between 0.1 and 0.5, the total pressure is above 20 bar, the total content of metal is above 20 wt % and the reaction temperature is above 225° C. In a particular embodiment, the support is $Al_2O_3$, the iron-nickel atomic ratio is about 0.3, the total pressure is about 30 bar, the total content of metal is above 20-25 wt % and the reaction temperature is about 300° C. Carrying out the process according to these specifications results in $CO_2$-conversions as high as 95%, with 100% selectivity to methane and with no formation of higher hydrocarbons.

The catalyst may be promoted with one or more elements from the lanthanide series (rare earth elements), preferably the oxide of elements selected from the group consisting of cerium (Ce), praseodymium (Pr), neodymium (Nd), promethium (Pm), samarium (Sm) and mixtures thereof. Hence, the catalyst may further contain above 3 wt % promoter, such as 5, 7, 10, 15 wt % or even higher, wherein the promoter is one or more oxides of elements selected from the group consisting of cerium, praseodymium, neodymium, promethium, samarium and mixtures thereof.

EXAMPLES

In the examples activity and selectivity of iron-nickel catalysts according to the invention in the methanation of carbon monoxide to methane were tested at different process conditions. Examples 1 to 21 and 23 were preformed at a total pressure of about 1 bar. In example 22 the pressure was 31 bar.

Example 1

A comparative Ni-containing catalyst was prepared using incipient wetness impregnation of spinel-type $MgAl_2O_4$ support having particle size from 0.25 mm to 0.5 mm and having pore volume of about 0.7 $cm^3/g$ and a surface area of about 70 $m^2/g$ with an aqueous solution of nickel nitrate ($Ni(NO_3)_2$) such that the resulting catalyst has about 2.5 wt % Ni. Prior to the impregnation the support was dried in the oven at 200° C. for 5 hours. A period of about 4 hours was allowed for the salt solution to fill the pores of the carrier. The impregnated spinel is then dried at room temperature for 12 hours and then heated in air up to 500° C. with a heating rate of 2.5° C. per minute and kept at 500° C. for 5 hours.

Example 2

A comparative catalyst is prepared following the method of Example 1 except that nickel nitrate is replaced by the iron nitrate, $Fe(NO_3)_3$, to obtain a catalyst containing about 2.5 wt % Fe.

Example 3

A catalyst is prepared using incipient wetness impregnation of support as in Example 1 except that the concentration of $Ni(NO_3)_2$ is decreased to obtain 2.1875 wt % Ni in the resulting catalyst. After impregnation the sample was dried at room temperature for 12 hours and impregnated with the solution of $Fe(NO_3)_3$ to obtain an iron concentration in the resulting catalyst of about 0.3125 wt %. Impregnated catalyst is then dried at room temperature for 12 hours and then heated in air up to 500° C. with a heating rate of 2° C. per minute and kept at 500° C. for 5 hours.

Example 4

A catalyst is prepared following the method of Example 3 except that the concentration of $Ni(NO_3)_2$ is decreased to obtain 1.875 wt % Ni in the resulting catalyst, while the concentration of $Fe(NO_3)_3$ is increased to obtain 0.625 wt % Fe in the resulting catalyst. FIG. 1 shows the performance of this catalyst at different temperatures.

Example 5

A catalyst is prepared following the method of Example 3 except that the concentration of $Ni(NO_3)_2$ is decreased to obtain 1.5625 wt % Ni in the resulting catalyst, while the concentration of $Fe(NO_3)_3$ is increased to obtain 0.9375 wt % Fe in the resulting catalyst.

Example 6

A catalyst is prepared following the method of Example 3 except that the concentration of $Ni(NO_3)_2$ is decreased to obtain 1.25 wt % Ni in the resulting catalyst, while the concentration of $Fe(NO_3)_3$ is increased to obtain 1.25 wt % Fe in the resulting catalyst.

Example 7

A catalyst is prepared following the method of Example 3 except that the concentration of $Ni(NO_3)_2$ is decreased to obtain 0.625 wt % Ni in the resulting catalyst, while the concentration of $Fe(NO_3)_3$ is increased to obtain 1.875 wt % Fe in the resulting catalyst.

Example 8

A series of the catalyst was prepared similar to the Examples 1-7 except that total concentrations of metal in the resulting catalysts were four times higher (10 wt %).

Example 9

A series of the catalyst was prepared similar to that described in Example 4 except that total concentration of Ni+Fe metals in the resulting catalyst was 2.5; 5.0; 10 and 20 wt %.

Example 10

A series of the catalyst was prepared similarly to those catalysts discussed in Examples 1-7 except that alumina oxide $Al_2O_3$ with a specific surface area of about 150 m²/g and with a particle size of 0.25-0.5 mm was used as a support instead of $MgAl_2O_4$ spinel.

Example 11

A series of the catalyst was prepared similar to those in Examples 1-7 except that total concentration of metal in the resulting catalysts were higher (10 wt %).

Example 12

A series of the catalyst was prepared similar to the catalyst series in Example 10, but containing 22-24 wt % metal and with a nickel content of 99.4-67.2% of the metal with the rest as iron.

Example 13

A series of the catalyst was prepared similar to the Examples 1-7 except that silica oxide $SiO_2$ with a specific surface area of about 300 m²/g and particle size 0.25-0.5 mm was used as a support instead of $MgAl_2O_4$ spinel.

Example 14

A series of the catalyst was prepared similar to the Example 10 except that total concentration of metal in the resulting catalyst was four times higher (10 wt %).

Example 15

The performance of the catalysts prepared in the Examples 1-7 was tested in the fixed-bed quartz U-tube reactor. 150 mg of the catalyst (fraction 0.25-0.50 mm) is placed into the quartz U-tube reactor between two layers of quartz wool. The flow of 2 vol % CO in $H_2$ is then admitted to the reactor at an hourly space velocity of about 40 000 h−1 and reaction pressure between 1.1-1.3 Bar. Prior to the activity measurements the catalyst are reduced at 500° C. in hydrogen for 4 hours and then the temperature is lowered, while the CO methane and other product concentrations are monitored.

Example 16

The blank CO hydrogenation activity is measured as in the Example 15 except that no catalyst is loaded into the reactor. No CO conversion was detected at the given conditions and at temperatures up to 500° C.

Example 17

The comparison of the results of methanation activity for several catalysts prepared as in Examples 1-7 is given in the Table 1. From this data it is clearly seen that optimized bimetallic Fe—Ni catalysts are better than traditional monometallic Ni-based catalyst and that particularly high methanation activities (measured as % CO-conversion) are obtained where the iron-nickel atomic ratio (approximately equal to the weight ratio:atomic ratio=weight ratio×1.05) is between 0.1 and 0.5.

Example 18

The comparison of the results of methanation activity and selectivity for several catalysts prepared as in Example 8 is given in Table 2. From the data in Table 1 and Table 2 it is clearly seen that bimetallic Fe—Ni catalysts with Fe to Ni ratio 1:1 and 1:3 are better than traditional monometallic Ni-based catalysts. Particularly, high methanation activity is found with the bimetallic Fe—Ni catalyst with Fe to Ni ratio of 1:3 (iron-nickel atomic ratio of about 0.3).

Example 19

The comparison of the results of methanation activity and selectivity for catalysts prepared as in Example 9 is given in Table 3 for $Ni_3Fe$ catalysts, i.e. bimetallic Fe—Ni catalyst with Fe to Ni ratio of 1:3 (iron-nickel atomic ratio of about 0.3). From these data it is clearly seen that optimal catalytic performance is achieved at higher total metal loadings.

Example 20

The comparison of the results of methanation activity and selectivity for several catalysts prepared as in Example 10 is given in the Table 4. From these data it is clearly seen that in the case of $Al_2O_3$ support bimetallic Fe—Ni catalysts with Fe to Ni ratios of 1:1 and 1:3 are also more active and in this case selective than traditional monometallic Ni-based catalyst. The data of Table 4 and Table 3 show that increased selectivity to methane is achieved when using $Al_2O_3$ compared to when using $MgAl_2O_4$ as carrier.

Example 21

The performance of the catalysts prepared in Example 12 was tested in the fixed bed tubular steel reactor at low pressure. 40 mg of the catalyst (fraction 0.25-0.5 mm) together with 260 mg of inert material (the $MgAl_2O_4$ material described in Example 1) is placed into the reactor. A gas mixture of 9 vol % $CO_2$ in $H_2$ is admitted to the reactor at an hourly space velocity of about 440.000 h−1 and a reaction pressure in the range 1.0-1.1 bar. Prior to the activity measurements, the catalyst is reduced at 550° C. for 4 hours and then the temperature is lowered, while $CO_2$, CO, methane and other product concentrations are monitored by gas chromatography. Comparison of the methanation activities for the four catalysts prepared in Example 12 are given in Table 5. From these data it is clearly seen that bimetallic Fe—Ni catalyst is more active then the traditional monometallic Ni-based catalyst. Particularly, high methanation activity ($CO_2$-conversion %) is found with the bimetallic Fe—Ni catalyst with Fe to Ni ratio of 1:3 (iron-nickel atomic ratio of about 0.3).

Example 22

The performances of two of the catalysts prepared in the Example 12 were tested in the fixed-bed tubular steel reactor at high pressure. 300 mg of the catalyst (fraction 0.25-0.5 mm) was placed into the reactor. A flow of 4 vol % $CO_2$ in $H_2$ was admitted into the reactor at an hourly space velocity of about 800.000 h−1 and reaction pressure of 31 bar. Prior the activity measurements the catalyst are reduced at 550° C. for 4 hours and then the temperature is lowered, while the $CO_2$, CO, methane and other product concentrations are monitored by gas chromatography. The comparison of the results for the methanation activity for two catalysts prepared as in Examples 12 is given in Table 6. It is clear that the bimetallic Fe—Ni catalyst is more active than the traditional monometallic Ni-based catalyst at high pressures. Furthermore, the formation of higher hydrocarbons is negligible (high selectivity). Particularly high methanation activity ($CO_2$-conversion %) is found with the bimetallic Fe—Ni catalyst with Fe to Ni ratio of 1:3 (iron-nickel atomic ratio of about 0.3). The data of Table 5 and 6 shows that a significantly higher methanation activity is achieved when increasing the pressure from about 1 bar to about 30 bar, despite of the much higher space velocity used in the catalysts of Table 6. This effect is even more pronounced when the reaction temperature is increased to about 300° C.

Example 23

The activity of the catalysts prepared in Example 11 was measured similar to Example 15 except that 2 vol % $CO_2$ was added to the reaction mixture. The comparison of the results for the methanation activity and selectivity is given in Table 7. It is clearly seen that alloying of metal leads to the significantly improved activity of the catalyst in comparison with traditional catalyst and that particularly high methanation activity is found with the bimetallic Fe—Ni catalyst with Fe to Ni ratio of 1:3 (iron-nickel atomic ratio of about 0.3).

Example 24

Figure 3:
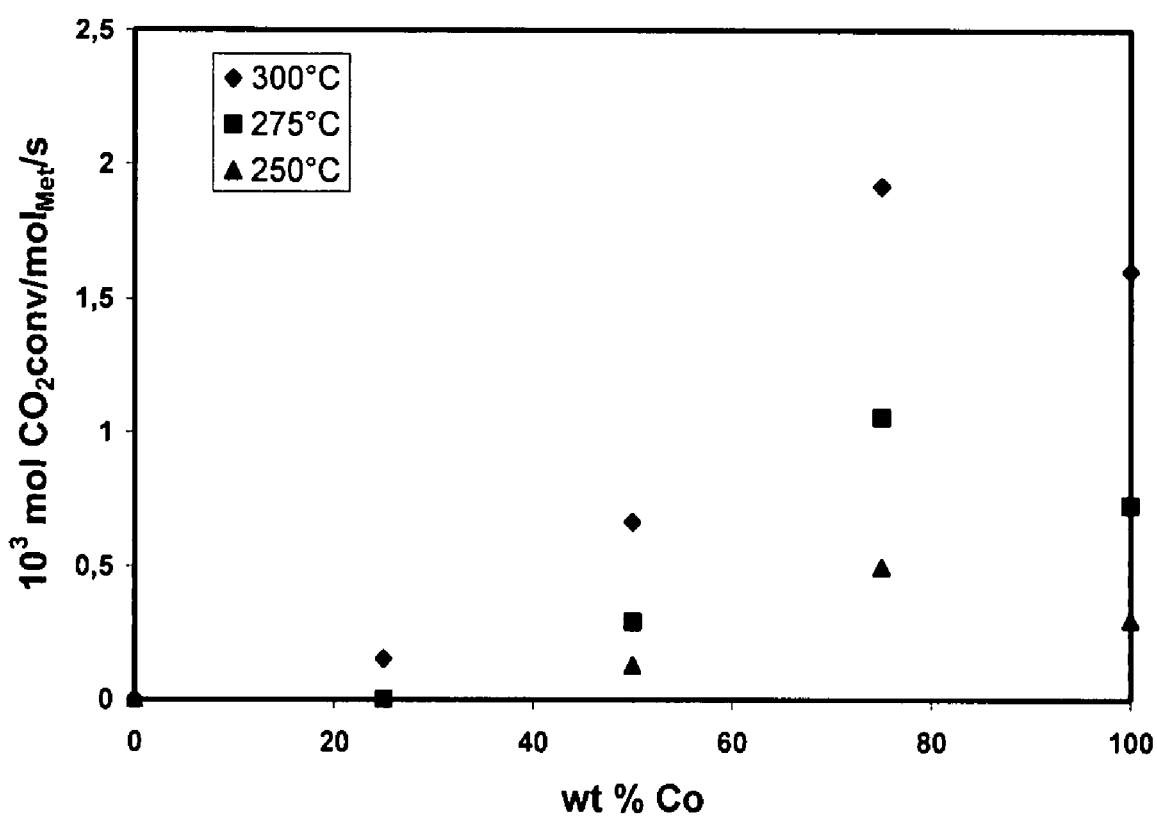
FIG. 3 is a graphical presentation of CO hydrogenation activity for iron-cobalt catalysts. The total metal loading is the same for all presented catalyst and is about 7.5 wt %

A series of the catalyst was prepared similarly to those catalysts discussed in Examples 1-7 except that alumina oxide $Al_2O_3$ with a specific surface area of about 150 m²/g and with a particle size of 0.25-0.5 mm was used as a support instead of $MgAl_2O_4$ spinel that $Co(NO_3)_2$ was used instead of $Ni(NO_3)_2$ and that the total metal loading was 7.5 wt %. The results for the iron-cobalt catalysts are presented in Table 8 and FIG. 3. Particularly high methanation activity is found with the bimetallic Fe—Co catalyst with iron-cobalt atomic ratio of 1:3 (approximately equal to the weight ratio:atomic ratio=weight ratio×1.05).

Table 1. Catalytic performance of mono and bimetallic Ni—Fe catalysts supported on $MgAl_2O_4$ with total metal loading 2.5 wt %. Gas composition: 2% CO balanced with $H_2$. GHSV=40.000 h⁻¹.

TABLE 1

| Temperature, ° C. | Metal content in the catalyst, wt % | | CO conversion, % | Selectivity to $CH_4$, % |
|---|---|---|---|---|
| | Ni | Fe | | |
| 250 | 2.5 | — | 7.2 | 97.6 |
| | 2.1875 | 0.3125 | 11.6 | 94.1 |
| | 1.875 | 0.625 | 24.3 | 93.4 |
| | 1.25 | 1.25 | 7.2 | 91.2 |
| | — | 2.5 | 0.23 | 58.5 |
| 275 | 2.5 | — | 23.3 | 98.7 |
| | 2.1875 | 0.3125 | 34.3 | 96.3 |
| | 1.875 | 0.625 | 67.4 | 96.3 |
| | 1.25 | 1.25 | 25.5 | 92.6 |
| | — | 2.5 | 1.3 | 71.1 |
| 300 | 2.5 | — | 64.8 | 99.4 |
| | 2.1875 | 0.3125 | 78.6 | 98.0 |
| | 1.875 | 0.625 | 96.4 | 97.7 |
| | 1.25 | 1.25 | 63.1 | 94 |
| | — | 2.5 | 4.7 | 77.5 |

Table 2. Catalytic performance of mono and bimetallic Ni—Fe catalysts supported on $MgAl_2O_4$ with total metal loading 10 wt %. Gas composition: 2% CO balanced with $H_2$. GHSV=40.000 h⁻¹.

TABLE 2

| Temperature, ° C. | Metal content in the catalyst, wt % | | CO conversion, % | Selectivity to $CH_4$, % |
|---|---|---|---|---|
| | Ni | Fe | | |
| 225 | 10.0 | — | 7.97 | 84.8 |
| | 7.5 | 2.5 | 38.6 | 90.7 |
| | 5.0 | 5.0 | 40.5 | 85.5 |
| | 2.5 | 7.5 | 16.3 | 75.7 |
| | — | 10.0 | 1.6 | 55.7 |
| 250 | 10.0 | — | 34.6 | 94.2 |
| | 7.5 | 2.5 | 99.5 | 96.4 |
| | 5.0 | 5.0 | 95.4 | 92.9 |
| | 2.5 | 7.5 | 39.0 | 75.7 |
| | — | 10.0 | 4.4 | 68.1 |

Table 3. Catalytic performance bimetallic $Ni_3Fe$ catalysts with different total metal loadings supported on $MgAl_2O_4$. Gas composition: 2% CO balanced with H2. GHSV=40.000 h⁻¹.

TABLE 3

| Temperature, ° C. | Metal content in the catalyst, wt % | | CO conversion, % | Selectivity to $CH_4$, % |
|---|---|---|---|---|
| | Ni | Fe | | |
| 200 | 1.87 | 0.63 | 0.9 | 89.2 |
| | 3.75 | 1.25 | 6.5 | 86.8 |
| | 7.50 | 2.50 | 8.6 | 82.1 |
| | 15.00 | 5.00 | 19.0 | 89.7 |
| 225 | 1.87 | 0.63 | 4.5 | 90.7 |
| | 3.75 | 1.25 | 17.8 | 91.1 |
| | 7.50 | 2.50 | 38.6 | 90.7 |
| | 15.00 | 5.00 | 97.7 | 96.7 |
| 250 | 1.87 | 0.63 | 15.1 | 93.3 |
| | 3.75 | 1.25 | 66.1 | 95.3 |
| | 7.50 | 2.50 | 99.5 | 96.4 |
| | 15.00 | 5.00 | 99.9 | 98.4 |

Table 4. Catalytic performance of mono and bimetallic Ni—Fe catalysts supported on $Al_2O_3$ with total metal loading 10 wt %. Gas composition: 2% CO balanced with $H_2$. GHSV=40.000 h⁻¹.

TABLE 4

| Temperature, °C. | Metal content in the catalyst, wt % | | CO conversion, % | Selectivity to CH$_4$, % |
| --- | --- | --- | --- | --- |
| | Ni | Fe | | |
| 225 | 10.0 | — | 21.1 | 96.0 |
| | 7.5 | 2.5 | 25.6 | 97.5 |
| | 5.0 | 5.0 | 38.2 | 96.1 |
| | 2.5 | 7.5 | 11.1 | 88.9 |
| | — | 10.0 | 1.4 | 85.5 |
| 250 | 10.0 | — | 72.5 | 99.0 |
| | 7.5 | 2.5 | 85.8 | 99.1 |
| | 5.0 | 5.0 | 99.5 | 98.6 |
| | 2.5 | 7.5 | 27.4 | 90.2 |
| | — | 10.0 | 4.3 | 88.6 |

Table 5. Catalytic performance of mono and bimetallic Ni—Fe catalysts supported on Al$_2$O$_3$ with total metal loading 22-24 wt %. Gas composition: 9% CO balanced with H2. GHSV=440.000 h$^{-1}$. The selectivity was not studied in these experiments.

TABLE 5

| Temperature, °C. | Metal content in the catalyst, wt % | | CO$_2$ conversion, % |
| --- | --- | --- | --- |
| | Ni | Fe | |
| 225 | 23.9 | — | 1.1 |
| | 20.2 | 3.47 | 1.3 |
| | 17.5 | 5.85 | 1.7 |
| | 14.8 | 7.24 | 1.5 |
| 250 | 23.9 | — | 2.7 |
| | 20.2 | 3.47 | 3.8 |
| | 17.5 | 5.85 | 4.6 |
| | 14.8 | 7.24 | 4.3 |
| 275 | 23.9 | — | 6.4 |
| | 20.2 | 3.47 | 9.6 |
| | 17.5 | 5.85 | 10.9 |
| | 14.8 | 7.24 | 10.1 |
| 300 | 23.9 | — | 13.3 |
| | 20.2 | 3.47 | 19.7 |
| | 17.5 | 5.85 | 21.5 |
| | 14.8 | 7.24 | 20.0 |

Table 6. Catalytic performance of mono and bimetallic Ni—Fe catalysts supported on Al$_2$O$_3$ with total metal loading of 22-24 wt %. Gas composition: 4% CO$_2$ balanced with H$_2$. GHSV=780.000 h$^{-1}$ and a pressure of 31 bar. Methane was detected as the only product.

TABLE 6

| Temperature, °C. | Metal content in the catalyst, wt % | | CO2 conversion, % | Selectivity to CH$_4$, % |
| --- | --- | --- | --- | --- |
| | Ni | Fe | | |
| 227 | 23.9 | — | 4.5 | 100.0 |
| 258 | 23.9 | — | 13.6 | 100.0 |
| 302 | 23.9 | — | 54.8 | 100.0 |
| 227 | 17.5 | 5.85 | 5.4 | 100.0 |
| 245 | 17.5 | 5.85 | 12.4 | 100.0 |
| 260 | 17.5 | 5.85 | 22.7 | 100.0 |
| 305 | 17.5 | 5.85 | 95.0 | 100.0 |

Table 7. Catalytic performance of mono and bimetallic Ni—Fe catalysts supported on Al$_2$O$_3$ with total metal loading 10 wt %. Gas composition: 2% CO, 2% CO$_2$, balanced with H$_2$. GHSV=40.000 h$^{-1}$.

TABLE 7

| Temperature, °C. | Metal content in the catalyst, wt % | | CO Conversion, % | CO2 Conversion, % | Selectivity to CH$_4$, % |
| --- | --- | --- | --- | --- | --- |
| | Ni | Fe | | | |
| 280 | 10.0 | — | 50.6 | 0.0 | 99.4 |
| | 7.5 | 2.5 | 97.5 | 61.7 | 99.5 |
| | 5.0 | 5.0 | 35.6 | 1.2 | 95.7 |
| | 2.5 | 7.5 | 0.0 | 0.0 | — |
| | — | 10.0 | 0.0 | 0.0 | — |
| 300 | 10.0 | — | 89.2 | 1.1 | 99.8 |
| | 7.5 | 2.5 | 98.5 | 91.7 | 99.7 |
| | 5.0 | 5.0 | 78.4 | 5.2 | 96.2 |
| | 2.5 | 7.5 | 0.1 | 1.7 | 92.4 |
| | — | 10.0 | 0.0 | 0.0 | — |
| 320 | 10.0 | — | 99.8 | 12.5 | 99.9 |
| | 7.5 | 2.5 | 99.9 | 98.6 | 99.9 |
| | 5.0 | 5.0 | 99.9 | 37.9 | 98.24 |
| | 2.5 | 7.5 | 1.8 | 5.0 | 91.7 |
| | — | 10.0 | 0.0 | 0.0 | — |

Table 8. Catalytic performance of mono and bimetallic Fe—Co catalysts supported on Al$_2$O$_3$ with total metal loading 7.5 wt %. Gas composition: 2% CO balanced with H$_2$.

TABLE 8

| Temperature, °C. | Co wt % | Fe wt % | CO$_2$ to CH$_4$ conv. | GHSV h$^{-1}$ |
| --- | --- | --- | --- | --- |
| 250 | 7.5 | 0.0 | 0.019 | 180400 |
| | 5.7 | 1.9 | 0.032 | 150333 |
| | 3.8 | 3.8 | 0.008 | 150333 |
| | 1.9 | 5.7 | 0.000 | 60133 |
| | 0.0 | 7.5 | 0.000 | 60133 |
| 275 | 7.5 | 0.0 | 0.046 | 180400 |
| | 5.7 | 1.9 | 0.068 | 150333 |
| | 3.8 | 3.8 | 0.019 | 150333 |
| | 1.9 | 5.7 | 0.000 | 60133 |
| | 0.0 | 7.5 | 0.000 | 60133 |
| 300 | 7.5 | 0.0 | 0.102 | 180400 |
| | 5.7 | 1.9 | 0.123 | 150333 |
| | 3.8 | 3.8 | 0.043 | 150333 |
| | 1.9 | 5.7 | 0.010 | 60133 |
| | 0.0 | 7.5 | 0.000 | 60133 |

The invention claimed is:

1. A process for hydrogenation of carbon oxides comprising contacting a gas mixture containing carbon oxides and hydrogen in which the concentration of carbon oxides is below 5 vol % and the hydrogen concentration above 40 vol % with a fixed-bed catalyst comprising bimetallic iron-nickel alloy as the active catalytic material supported on a carrier of an oxide, in which the iron-nickel atomic ratio is between 0.1 and 0.8.

2. A process for hydrogenation of carbon oxides comprising contacting a gas mixture containing carbon oxides and hydrogen in which the concentration of carbon oxides is below 5 vol % and the hydrogen concentration above 40 vol % with a fixed-bed catalyst comprising bimetallic iron-nickel alloy with iron-nickel atomic ratio between 0.1 and 0.8 or bimetallic iron-cobolt atomic ratio between 0.05 and 2 as the active catalytic material supported on a carrier of an oxide, and wherein the total pressure is above 20 bar.

3. The process of claim 1, wherein the carrier is formed to have a surface area greater than 20 m$^2$/g.

4. The process of claim 1, wherein the bimetallic catalyst is impregnated onto the carrier using precursors that transform into oxide upon heating in air.

5. The process of claim 1, wherein the carrier is selected from the group consisting of $MgAl_2O_4$, $Al_2O_3$, $SiO_2$, $ZrO_2$, $TiO_2$ and mixtures thereof.

6. The process of claim 1, wherein the content of the bimetallic active catalytic material is between 2 wt % and 50 wt %.

7. The process of claim 1, wherein the iron-nickel atomic ratio is between 0.2 and 0.5.

8. The process of claim 1, wherein the iron-nickel atomic ratio is about 0.3.

9. The process of claim 7, wherein the carrier is $Al_2O_3$.

10. The process of claim 9, wherein the reaction temperature is between 200° C. and 400° C.

11. The process of claim 2, wherein the total pressure is in the range 20 to 80 bar.

* * * * *